United States Patent [19]

Young

[11] 4,401,680

[45] Aug. 30, 1983

[54] BIOCONVERSION OF CEREAL GRAIN STRAWS TO PROTEIN-ENRICHED PRODUCT

[75] Inventor: Murray M. Young, Waterloo, Canada

[73] Assignee: University of Waterloo, Waterloo, Canada

[21] Appl. No.: 240,586

[22] Filed: Mar. 4, 1981

Related U.S. Application Data

[63] Continuation-in-part of Ser. No. 3,998, Jan. 17, 1979, abandoned.

[51] Int. Cl.$^3$ .................................................. A23K 1/00
[52] U.S. Cl. ........................................ 426/53; 426/55; 426/56; 426/636; 426/807
[58] Field of Search .................. 426/53, 49, 55, 56, 426/623, 635, 636, 807; 435/68, 253, 255

[56] References Cited

U.S. PATENT DOCUMENTS

| | | | |
|---|---|---|---|
| 3,761,355 | 9/1973 | Callihan et al. | 435/68 |
| 3,838,199 | 9/1974 | Coe et al. | 426/55 X |
| 3,875,317 | 4/1975 | Ferguson | 426/635 |
| 3,937,845 | 2/1976 | Han et al. | 426/53 |
| 3,973,043 | 8/1976 | Lynn | 426/56 |
| 4,062,727 | 12/1977 | Srinivasan et al. | 435/253 |
| 4,082,859 | 4/1978 | Katzen | 426/807 |
| 4,119,495 | 10/1978 | Belyaev et al. | 435/255 |

OTHER PUBLICATIONS

Moo Young et al., "SCP Production by *Chaetomium cellulolyticum* a New Thermosolvent Cellulolytic Fungus" Chemical Abstracts vol. 87 (1977) Abs. No. 15395j.

*Primary Examiner*—R. B. Penland
*Attorney, Agent, or Firm*—Sim & McBurney

[57] ABSTRACT

Cereal grain straws are converted into protein-enriched products having significnt amounts of microbial biomass in the form of the fungus, *Chaetomium cellulolyticum*.

11 Claims, No Drawings

BIOCONVERSION OF CEREAL GRAIN STRAWS TO PROTEIN-ENRICHED PRODUCT

REFERENCE TO RELATED APPLICATION

This application is a continuation-in-part of copending United States patent application Ser. No. 003,998 filed Jan. 17, 1979 (now abandoned).

FIELD OF INVENTION

The present invention relates to the conversion of agricultural cellulosic residues by a fermentation process into products which contain microbial biomass, such products being useful as animal or human food for their protein and other nutritive values. In the following description concentrations of substances are expressed as W/V (for weight per unit volume of total mixture), as V/V (for volume per unit volume of total mixture), as W/W (for weight per unit weight of total mixture), or as DM (for weight per unit weight of total mixture on a dry matter basis).

BACKGROUND OF THE INVENTION

Vast quantities of cellulosic materials occur universally as surplus and waste residues of agricultural operations. In particular, they occur in the form of straws of cereal grains, for example, wheat, barley, corn rice, oats and rye (sometimes termed stovers, for example, cornstover). Basically, these materials contain cellulose, usually in combination with significant amounts of hemicellulose and smaller amounts of lignin. Because of their carbohydrate content, these materials represent potentially valuable renewable resources for animal feed production.

Various known processes have been proposed or used to convert various cellulosic materials into products which are purported to be suitable, as substitutes for soymeal and similar protein-rich substances, for animal feed protein rations through the utilization of the cellulose as the carbon source for the fermentation of microorganisms to protein-enriched biomass. Cellulosic materials are generally resistant to direct solid phase utilization in such fermentations and require pretreatment to render the cellulose in a form which is utilizable by the microorganism as a carbon source.

In one such prior art process, yeasts are cultivated on liquid monomeric sugar solutions which are produced by chemical hydrolysis of the hemicellulose and/or cellulose components of the cellulosic material. A typical example of this type of process is that described in Han et al U.S. Pat. No. 3,937,845, wherein there is described the hydrolysis of straw using sulphuric acid and the subsequent utilization of the hydrolyzed sugars as a carbon source for the growth of yeasts, together with *Trichoderma viride,* to form animal feed.

In another prior art process, the cellulose material is initially pretreated to depolymerize or degrade lignin in the cellulosic material before cultivation of cellulase-elaborating bacteria of the genus Cellulomonas on the pretreated material. The pretreatment involves the use of aqueous sodium hydroxide solution of concentration from 2 to 50% by weight at temperatures from 25° C. to 100° C. and treatment time of 15 to 90 minutes. Such a process is described in Callihan et al U.S. Pat. No. 3,761,355 and Srinivasan et al U.S. Pat. No. 4,062,727.

Prior art procedures have, in general, suffered from a number of drawbacks which are considered highly undesirable. Processing costs tend to be high because conversion rates are low, and/or extreme pretreatment conditions of temperature and/or pressure are required to be utilized for pretreatment of the cellulosic material, and/or the pretreatment liquor must be discarded. In some cases, the product is not suitable as animal feed protein ration, owing to a too low protein content and a too poor protein quality. In addition, some products are unsuitable owing to toxicity and indigestibility problems.

It has previously been disclosed by the inventor herein and his coworkers, in an article entitled "SCP Production by *Chaetomium cellulolyticum,* a New Thermotolerant Cellulolytic Fungus", published in Biotechnology and Bioengineering, vol. XIX, pages 527–538 (1977), that *Chaetomium cellulolyticum* (ATCC No. 323319), a (then) newly-isolated cellulolytic fungus, showed 50 to 100% faster growth rate and over 80% more final biomass-protein formation than *Trichoderma viride,* a well-known high cellulase-producing cellulolytic organism, when certain cellulose materials were used as the sole carbon source in the fermentation media, and further the amino acid composition of the product compares more favorably with alfalfa and soya meal than *Trichoderma viride.*

The cellulosic materials included sawdust, a forestry residue material, and this material was subjected to partial delignification by treatment with 1% NaOH for 1 hour at boiling followed by boiling for 1 hour in peracetic acid. This severe pretreatment procedure was chosen since it was commonly used to treat cellulosic materials to prepare the same for use of the carbon sources in the fermentation of other microorganisms, such as Cellulomonas species. In addition, the pretreatment liquor was discarded prior to fermentation of the solids.

SUMMARY OF INVENTION

It has now been found that a different process may be used to effect fermentation of solid phase cereal grain straws in a culture of the fungus, *Chaetomium cellulolyticum,* to products containing significant proportions of microbial biomass. In the present invention, a mild treatment of the cereal grain straw is effected, by either a simple sterilization process in the presence of dilute alkali, or by anerobic thermophilic fermentation, to soften the straw and render it susceptible to fermentation by the fungus. The liquid phase from the softening treatment of the straw is retained in the fermentation medium.

This process contrasts markedly with the prior art fermentation of *Chaetomium cellulolyticum* wherein a cellulosic material was used as the carbon source, wherein the pretreatment was severe and the pretreatment liquor was discarded and not used in the fermentation medium. The process of the invention enables proteinaceous material to be formed from an agricultural waste material, namely, cereal grain straw in a much shorter period of time, in the presence of the pretreatment liquor, under milder chemical treatment conditions and in more economic manner than has heretofore been the case.

GENERAL DESCRIPTION OF INVENTION

Raw Material

The present invention is concerned with the conversion of cereal grain straws into a microbial biomass product. Cereal grain straws to which the invention is applicable include rice, oats, barley, wheat and corn.

The ability to use these normally waste materials to form nutritionally useful protein-enriched products is a significant environmental pollution control factor of this invention.

The Process

The process of the present invention consists essentially of three steps: (1) pretreatment of the cereal grain straw, (2) aerobic fermentation of a mixture of the pretreated cereal grain straw, the pretreatment liquor and a nutrient supplement solution and (3) separation of the solids from the fermented mixture. Optionally, the separation solid product may be dried.

The pretreatment of the creal grain straw, which is one of the features which distinguishes the present invention from prior cellulosic fermentation processes, involves the utilization of one of three alternative procedures. The choice of procedure to be adopted depends on the prevailing economies of available resources.

The first two procedures involve simple sterilization of the cereal grain straw while in contact with alkali to soften the cereal grain straw to render the same susceptible to fermentation by the fungus. The alkali pretreatment is effected under those conditions of energy and time which are conventionally used for sterilization, with longer periods of time being required for lesser levels of energy, as is well known in the art.

The strength of alkali used depends on the proportion of microbial biomass, the hence protein content, of the product which is desired. A minimum pretreatment corresponds to a product containing at least about 5% DM of microbial biomass while the maximum pretreatment corresponds to a product containing 100% DM of biomass. Preferably, the pretreatment is effected to achieve a biomass content of about 20 to about 80% DM, (or about 9 to about 36% DM of protein).

In the first pretreatment procedure, hot alkali is used to achieve the sterilization and softening. The alkali usually is sodium hydroxide solution, although any other desired alkali may be utilized.

The sodium hydroxide is utilized in this procedure in a concentration which may range from about 0.25 to about 1.0% w/v NaOH and the pretreatment may be effected at any convenient temperature in the range from about 60° to about 121° C. The reaction time required to effect the pretreatment varies interdependently with the temperature and is usually in the range of from about 120 to about 15 minutes. A typical set of conditions is 121° C. for 20 minutes using 0.5% NaOH.

The second pretreatment procedure involves a combination of the use of cold alkali and gamma radiation. As in the first pretreatment procedure, the alkali usually is sodium hydroxide, although any other desired alkali may be utilized.

The sodium hydroxide solution is utilized in this second procedure in a concentration which may range from about 3 to about 6% w/w NaOH and at an ambient room temperature of about 15° to about 30° C. The gamma radiation may be applied at a dosage level of about 10 to about 50 megarads. The time required for pretreatment varies interdependently with the radiation dosage and is usually in the range of from about 120 to about 60 minutes. A typical set of conditions is 10 megarads for 120 minutes using 4% NaOH at 25° C. The source of gamma radiation may be any convenient gamma-ray-emitting material, and is conveniently a gamma-ray-emitting nuclear waste material.

The third pretreatment procedure involves thermophilic anaerobic digestion of the cereal grain straw using animal manure, such as cattle or swine manure. Such thermophilic anaerobic fermentation may be effected under conditions conventional for such fermentations, usually involving a temperature of about 50° to about 60° C. and a fermentation time of about 4 to 8 days, typically about 4 days at 55° C.

The latter pretreatment operation, nevertheless, is quite time consuming when compared with the alkali processes, although the procedure is quite practical where small quantities of cereal grain straw are to be processed, the coproduced methane gas is useful, and the energy sources for the alkali pretreatments may not be available.

The cellulosic material generally is particulated prior to commencement of the pretreatment and the pretreatment usually is effected at a solids concentration of about 5 to about 30% W/W. If used in granular form, the particles may have an average particle size in the range of about 1 to about 5 mm. If used in fibrous forms, fibre sizes up to 2 cm in length may be used.

Another significant feature of the process of this invention is that the slurry of pretreated cereal grain straw and pretreatment medium which results from the pretreatment step may be, and preferably is, used in the formation of the sterile fermentation medium. In prior procedures, the pretreatment medium has been discarded, presenting a potential pollution hazard and a waste of valuable nutrient materials, as explained in more detail below.

The slurry which results from the anaerobic fermentation step needs only to be sterilized for utilization as the fermentation medium in the fermentation step. The anaerobically fermented manure provides non-carbon nutrients while the anaerobically fermented cereal grain straw provides the carbon source.

As is well known in the fermentation art, certain essential elements are required to be present in a fermentation medium to achieve proper microbial growth. As used herein, the term "non-carbon nutrients" refers to the conventional nutrient elements other than carbon. The fermentation medium, to the extent that the nutrients are not provided by the pretreated cellulose material, is supplemented from an external source of non-carbon nutrients to provide an overall composition of mixture which conforms to conventional guidelines for fermentation medium.

It is well known that a microorganism will utilize the essential elements for its growth in specific proportions which vary to a minor degree from organism to organism, but generally the major elements of carbon, nitrogen, phosphorus and potassium are utilized in the ratio of C:N:P:K of 100:10:1:1 by weight, and hence this ratio typically is provided in a fermentation medium. The proportions of these elements may vary, however, but the organism will leave unutilized any excess proportion of any given element.

The non-carbon nutrients may be provided in the form of a sterile nutrient supplement solution from any convenient source, such as, a synthetic mixture of chemicals containing the non-carbon elements required for supplementation, for example, a fertilizer blend.

When the pretreatment medium is retained with the pretreated cereal grain straw in the case of alkali pretreatment procedures, this medium effectively provides all the non-carbon nutrient elements required for other than nitrogen, as a result of the solubilization of elements, such as, phosphorus and potassium from the straw during the pretreatment. It is possible, therefore, to satisfy the requirement for non-carbon nutrients from an external source by a simple nitrogen-containing chemical, such as, ammonium sulphate of urea.

The nutrient supplement solution may also be provided by an animal manure, such as, cattle or swine manure. The animal manure may be anaerobically predigested, if desired, to co-produce methane as a valuable fuel by-product, and then the whole of the sludge resulting from the predigestion is used both as the non-carbon and carbon nutrient sources.

The consistency of the resulting sterile slurry mixture of fermentation medium is designed to be suitable for conventional submerged fermentation techniques, such as, up to about 3% W/V solids. The fermentation may, however, be effected at any desired concentration allowable by conventional solid state fermentation techniques, at an overall solids concentration of generally up to about 30% W/W.

The fermentation medium is adjusted, if necessary, to a pH in the range of about 5 to about 8, particularly about 5 to about 7, and inoculated with the fungus, Chaetomium cellulolyticum. Aerobic fermentation is effected at a temperature of about 30° to about 40° C., typically around 37° C., using sterile air, typically supplied at a flow rate of 1 to 2 volumes of air per unit volume of medium per minute.

During the fermentation, the fungus uses the cereal grain straw to reproduce itself and generate cellulase-enzymes, which soften and thereby improve the digestibility of any solid cereal grain straw which remains unutilized. The fermentation is continued until the desired fungus growth has been effected, for example, for about 12 to about 24 hours, if conducted batchwise. In continuous operations, an average residence time of the mixture in the fermentor is typically 4 to 8 hours for adequate growth.

The rate of fermentation may be accelerated by from about 25 to 30% by the incorporation in the fermentation medium of small amounts, usually about 0.01 to about 0.03% W/V, of a carboxypolymethylene.

Following completion of the fermentation, the solid phase is separated from the liquid phase. The separated solid phase may be used as such, or the separated solid phase may be dried to a low moisture content, generally below about 10% W/W, typically about 8% W/W. The liquid phase may be reused, if desired.

The solid phase product contains Chaetomium cellulolyticum in variable quantities, depending on the extent and conditions of the pretreatment and the fermentation. The product contains at least about 5% DM of biomass, usually from about 20 to about 80% DM, and up to 100% DM, if desired. The remainder of the solid phase is unfermented cereal grain straw.

Chaetomium cellulolyticum used herein is a fungus freely available from the American Type Culture Collection (ATCC No. 32319) and has the following capabilities: (1) utilization of a variety of cellulosic as well as non-cellulosic carbohydrate materials as carbon nutrient for growth, (2) utilization of a variety of synthetic as well as non-synthetic mixtures as non-carbon nutrient supplement for growth, (3) growth over a range of pH of about 5 to 8, the optimal being about pH 5 for insoluble cellulose and about pH 7 for solubilized hemicellulose and, (4) growth over a range of temperature of about 30° C. to 45° C., the optimal being about 37° C.

The average composition of the fungus is as follows (%DM basis): 45% crude protein, 40% carbohydrates, 10% fats, 5% vitamins, minerals, etc. The following Table shows that the amino acid profile of the protein component of the fungus is nutritionally sound and is comparable with fodder yeast (C. utilis), soymeal protein and the UN-FAO reference protein for human nutrition.

TABLE

| Amino Acid | C. cellulolyticum | C. utilis | Soy-meal | FAO reference |
|---|---|---|---|---|
| Threonine | 6.1 | 5.5 | 4.0 | 2.8 |
| Valine | 5.8 | 6.3 | 5.0 | 4.2 |
| Cystine | 0.3 | 0.7 | 1.4 | 2.0 |
| Methionine | 2.3 | 1.2 | 1.4 | 2.2 |
| Isoleucine | 4.7 | 5.3 | 5.4 | 4.2 |
| Leucine | 7.5 | 7.0 | 7.7 | 4.8 |
| Tyrosine | 3.3 | 3.3 | 2.7 | 2.8 |
| Phenylalamine | 3.8 | 4.3 | 5.1 | 2.8 |
| Lysine | 6.8 | 6.7 | 6.5 | 4.2 |

The product of the process of the invention has been found by in-vivo and in-vitro feeding trials to be suitable as animal feed supplement.

The procedure of the invention, therefore, enables cereal grain straw to be converted to proteinaceous product for animal or human consumption in a unique procedure which is fundamentally different from prior cellulosic fermentation procedures.

EXAMPLES

The examples given below further illustrate the present invention. It should be understood that the invention is not limited to these particular examples.

Unless otherwise specified, the source of nutrient supplement to provide essential elements other than carbon for the fungal growth referred to in the examples below are as follows:

(1) Solution A. A synthetic aqueous solution of 2.35 g/l $(NH_4)_2 SO_4$.

(2) Solution B. A synthetic mixture containing in one liter of aqueous solution 2 g $KH_2PO_4$, 1.4 g $(NH_4)_2 SO_4$, 0.3 g urea, 0.3 g $MgSO_4.7H_2O$, 0.3 g $CaCl_2$, 5 mg $FeSO_4.7H_2O$, 1.6 mg $MnSO_4.H_2O$, 1.4 mg $ZnSO_4.7H_2O$, 2 mg $CoCl_2$.

(3) Solution C. A non-synthetic mixture of swine manure (feces plus urine) diluted with water to contain about 0.05% W/V inherent nitrogen, the other naturally-occurring ingredients being reduced accordingly, and enriched with 0.05% W/V added nitrogen as $(NH_4)_2SO_4$.

(4) Solution D. A non-synthetic mixture of cattle manure (feces plus urine) diluted with water to contain about 0.05% W/V inherent nitrogen, the other naturally-occurring ingredients being reduced accordingly, and enriched with 0.05% W/V added nitrogen as $(NH_4)_2SO_4$.

(5) Solution E. A non-synthetic mixture of a stabilized anaerobically-digested cattle manure, prediluted with water, containing about 0.1% W/V inherent nitrogen.

The inoculum for the fermentations referred to in the examples below was prepared as follows. The fungus Chaetomium cellulolyticum is grown in serial transfers from a glucose-based fermentation medium to the actual cellulosic-based medium, using well-known standard techniques. Visible microbial growth was allowed to develop for one day after which it was removed and disrupted under aseptic conditions in a blender resulting in a suspension of microbial pieces, typically containing about 5% W/V solids. A small amount of this suspension, typically 5% V/V of the medium to be fermented, constitutes the inoculum.

EXAMPLE 1

The fermentation medium was prepared by heating for 20 minutes with live steam at 121° C., a solid-liquid slurry consisting of 1% W/V solid particles of a sample of wheat straw (1 mm mesh size) in a solution containing 50% V/V of 0.5% W/V sodium hydroxide and 50% V/V Solution B. After cooling the prepared medium to 37° C. and adjusting the pH to 5 with 2 N $H_2SO_4$ solution, it was seeded with a 5% V/V inoculum and fermented at 37° C. with sterile air using standard submerged fermentation shake-flask techniques.

After a growth period of 20 hours, the fermented solids were removed by filtration and dried in an oven overnight at about 80° C. to a moisture content of about 10% DM. It was found that the microbial biomass content of the solids in the original fermentation medium increased from zero to 44% DM, corresponding to a crude protein content of about 20% DM, the balance being unfermented cellulosic material. In standard in-vivo feeding trials using rats, the product was found to be favourably comparable to casein for up to 20% DM protein replacements of casein which was used in the "control" diets, with respect to non-toxicity, non-teratogenecity, digestibility and protein utilization efficiency.

EXAMPLE 2

The experiment of Example 1 was repeated using standard submerged fermentation stirred-tank techniques. After a growth period of 26 hours, the microbial biomass content of the product was found to be 75% DM. The results attained in this example illustrate the usual substantial improvement in production obtainable from gas-sparged mechanically-stirred tank compared with the simpler surface aerated shake-flask technique.

EXAMPLE 3

The experiment of Example 1 was repeated but using Solution A instead of Solution B. After a growth period of 22 hours, the microbial biomass content of the product was found to be 57% DM. The results of this example illustrate that when the pretreatment medium is retained with the alkali-treated cereal grain straw, a simple nitrogen containing salt, i.e., Solution A, provides an adequate external source of nutrients. The other nutrients in Solution B do not significantly alter the results obtained.

EXAMPLE 4

The experiment of Example 1 was repeated using a sample of cornstover of average fibre lengths of about 1 cm as the cellulosic material. The fermentation was conducted for a growth period of 12 hours. The dried product contained 73% DM of the microbial biomass and its in-vitro digestibility was 68% DM.

EXAMPLE 5

The experiment of Example 1 was repeated using Solution D as the nutrient supplement in place of Solution B. After a growth period of 24 hours, the dried product was found to contain 71% DM of the microbial biomass.

EXAMPLE 6

A fermentation medium was prepared and fermented as described in Example 1 using Solution E as the nutrient supplement. After a growth period of 20 hours, the dried product was found to contain 66% DM of the microbial biomass.

EXAMPLE 7

The experiment of Example 1 was repeated using a sample of rice straw (average particle size of 1 mm mesh) as the cellulosic material. After a growth period of 24 hours, the product contained 71% microbial biomass.

EXAMPLE 8

The experiment of Example 1 was repeated using cornstover as the cellulosic material and carrying out the pretreatment with a 4% W/V sodium hydroxide solution in a 33.3% W/V slurry at room temperature subjected to a dosage of 12 megarads of gamma-irradiation (from a Cobalt-60 source). After a growth period of 24 hours, the microbial biomass content of the product was found to be 78% DM. This example illustrates the economic attractiveness of applying nuclear plant radioactive wastes in the pretreatment step.

EXAMPLE 9

A 2% W/V slurry of ground cornstover (average particle size of about 2 mm mesh) in a sample of swine manure was pretreated for 4 days in a stabilized conventional anaerobic biological digester utilizing the same manure type and operating under thermophilic conditions (55° C.). The resultant mixture was sterilized, inoculated and fermented as in Example 1. After a growth period of 24 hours, the microbial biomass content of the product was found to be 30% DM. This example illustrates the economic attraction of applying commonly-used procedures for anaerobically digesting organic wastes such as animal manures and food residues.

EXAMPLE 10

(a) A series of fermentation experiments was conducted using three different organisms, namely, *Chaetomium cellulolyticum* (Organism A), *Trichoderma viride* (Organism B) and *Phanerochaete chrysosporium* (Organism C). The latter two organisms were chosen since they are purported to be the most efficient converters of cellulosic solid materials into microbial protein.

In the experiments, cornstover of average fibre length of about 1 cm was used as the cellulosic material, and was pretreated as described in Example 1 and supplemented with nutrient solutions to provide fermentation media as follows:

Type I: Alkali-pretreated cornstover particles + Solution B

Type II: As type I + Solution E in place of Solution B

For each case, three batches of fermentation medium were inoculated with the organism and fermented using standard aerated shake-flask techniques at 37° C. and an initial pH of 5.

All three organisms grew according to the usual exponential and growth-saturated patterns and the rates and extents of microbial biomass protein formation were determined. The results are reproduced in the following Table I:

TABLE I

| Organism | Medium Type | Protein Productivity Relative to Organism A (%) | Maximum Protein Production Relative to Organism A (%) |
| --- | --- | --- | --- |
| A | I | 100 | 100 |
| B | I | 56 | 44 |
| C | I | 38 | 43 |
| A | II | 100 | 100 |
| B | II | 50 | 63 |
| C | II | 36 | 39 |

The results of the above Table I show that Chaetomium cellulolyticum is significantly more efficient than the other two organisms, in terms both of protein productivity rate and maximum protein production yield.

(b) A further set of experiments was conducted in which 0.1% W/V yeast extract was added to Solution B and the following conditions of temperature and pH for the various organism were used:

Organism A—37° C., pH 5
Organism B—30° C., pH 5
Organism C—37° C., pH 4.5

All three organisms grew according to the usual exponential and growth-saturated patterns and the results for the rates and extents of microbial biomass protein production are given in the following Table II:

TABLE II

| Organism | Medium Type | Protein Productivity Relative to Organism A (%) | Maximum Protein Production Relative to Organism A (%) |
| --- | --- | --- | --- |
| A | I | 100 | 100 |
| B | I | 69 | 65 |
| C | I | 46 | 75 |
| A | II | 100 | 100 |
| B | II | 95 | 59 |
| C | II | 84 | 81 |

The results of the above Table II show that, even in the presence of an expensive medium additive (yeast extract) which purportedly provides the "best" culture conditions for Organisms B and C, *Chaetomium cellulolyticum* significantly excelled in terms of the rate and extent of protein product formation.

EXAMPLE 11

Fermentations were carried out using pretreated comminuted wheat straw of 1 mm mesh size using *Chaetomium cellulolyticum* cultivated according to standard aerobic fermentation techniques at 37° C. and pH 5.5 using Solution B as the non-carbon nutrient supplement. In one case, the pretreatment was effected using 1% NaOH followed by peracetic acid, as described in the prior art Moo-Young et al article referred to above; in another case, the pretreatment was effected using 2.5% $H_2SO_4$ as described in the Han et al patent; and in a third case simple sterilizing pretreatment was carried out using 1% NaOH alone, in accordance with this invention.

The protein productivity (i.e., the rate of protein product) and the product protein content were compared for the prior art Moo-Young et al process and this invention, the results being reproduced in the following Table III:

TABLE III

| Pretreatment Method | Protein Productivity | Product Protein Content |
| --- | --- | --- |
| Moo-Young et al (i.e., NaOH + peracetic acid) | 100% | 100% |
| This invention (i.e., NaOH alone) | 95% | 95% |

These results show that the use of significantly milder pretreatment of the wheat straw in accordance with this invention does not significantly adversely affect the productivity and product protein content.

The protein productivity, product protein and product digestibility of the product produced according to this invention were compared with the product produce following the Han et al process. Those results are reproduced in the following Table IV:

TABLE IV

| Pretreatment Method | Protein Productivity | Product Protein Content | Product Digestibility |
| --- | --- | --- | --- |
| This invention (i.e., NaOH) | 100% | 100% | 100% |
| Han et al (i.e., 2.5% $H_2SO_4$) | 100% | 65% | 47% |
| This invention + 0.01% W/V Carbopol 934 | 125% | 100% | 100% |

The results set forth in Table IV demonstrate that, although the use of sulphuric acid pretreatment to solubilize the cellulosic material gave similar protein productivity to fermentation effected on mildly-pretreated material according to this invention, the protein content of the product and the protein digestibility of the product, as animal feed, are significantly less. In addition, when a small amount of Carbopol 934 (a high molecular weight carboxy polymethylene) was present in the fermentation medium, a 25% increase in fermentation rate was achieved.

In summary of this disclosure, the present invention, therefore, provides a procedure for converting certain agricultural residues, namely cereal grain straws, into products which contain a fungal microbial biomass, and useful as protein-enriched animal and human foodstuff. Modifications are possible within the scope of the invention.

What I claim is:

1. A process for forming a proteinaceous material from cereal grain straw, which consists of:
   (a) pretreating said cereal grain straw in particulated form with an aqueous sodium hydroxide solution at a concentration of about 0.25 to about 1.0% W/V NaOH at a temperature of about 60° to 121° C. for a time from about 120 to about 15 minutes sufficient to sterilize said straw and form a slurry of the heated straw and spent sodium hydroxide solution;
   (b) mixing said slurry with a non-carbon fermentation nutrient chemical solution to form a sterile fermentation medium having a solids concentration of up to about 30% W/W;
   (c) aerobically fermenting said pretreated straw of step (a) in said fermentation medium of step (b) by the fungus, *Chaetomium cellulolyticum*, at a pH of about 5 to about 7 at a temperature of about 30° to about 40° C. for a time sufficient to provide a fermented solid mass consisting of about 20 to about 80% DM of the fungus and the balance of unfermented cellulosic material; and
(d) separating said solid mass from the fermentation medium.

2. The process of claim 1, wherein said cereal grain straw is selected from the group consisting of wheat, barley, corn, rice, oats and rye.

3. The process of claim 1 wherein said heating is effected at a temperature of about 120° C. for about 20 minutes using 0.5% W/V NaOH solution.

4. A process for forming a proteinaceous material from cereal grain straw, which consists of:
(a) pretreating said cereal grain straw in particulated form with an aqueous sodium hydroxide solution at a concentration of about 3 to about 6% W/W NaOH at a temperature of about 15° to about 30° C. while being subjected to gamma radiation at a dosage level of about 10 to about 50 megarads for a time of about 120 to about 60 minutes sufficient to sterilize said straw and form a slurry of the pretreated straw and spent sodium hydroxide solution;
(b) mixing said slurry with a non-carbon fermentation nutrient chemical solution to form a sterile fermentation medium having a solids concentration of up to about 30% W/W;
(c) aerobically fermenting said pretreated straw of step (a) in said fermentation medium of step (b) by the fungus, Chaetomium cellulolyticum, at a pH of about 5 to about 7 at a temperature of about 30° to about 40° C. for a time sufficient to provide a fermented solid mass consisting of about 20 to about 80% DM of the fungus and the balance of unfermented cellulosic material; and
(d) separating said solid mass from the fermentation medium.

5. The process of claim 4 wherein said pretreatment is effected at a temperature of about 25° C. for about 120 minutes at an applied gamma radiation of 10 megarads using about 4% W/W NaOH solution.

6. A process for forming a proteinaceous material from cereal grain straw, which consists of:
(a) pretreating the cereal straw in particulate form by thermophilic anaerobic fermentation using animal manure at a temperature of about 50° to about 60° C. for about 4 to 8 days to form a fermentation medium having a solids concentration of up to about 30% W/W and containing a solid phase of thermophilically anaerobically fermented cereal straw and sufficient nutrient elements to effect fungal fermentation;
(b) sterilizing said fermentation medium;
(c) inoculating said fermentation medium with a culture of the fungus, Chaetomium cellulolyticum;
(d) aerobically fermenting said fungus of step (c) in said fermentation medium of step (a) at a pH of about 5 to about 7 at a temperature of about 30° to about 40° C. for a time sufficient to provide a fermented solid mass consisting of about 20 to about 80% DM of the fungus and the balance of unfermented cellulosic material; and
(e) separating said solid mass from the fermentation medium.

7. The process of claim 6 wherein said animal manure is swine manure.

8. The process of claim 1 or 4, wherein the non-carbon nutrient comprises nitrogen as the sole element.

9. The process of claim 1 or 6, wherein said separated solid phase is dried to a moisture content of less than about 10% W/W.

10. The process of claim 1, 4 or 6, wherein said fermentation medium contains about 0.01 to about 0.3% W/V of a carboxy polymethylene.

11. The process of claim 1, 4 or 6 wherein the pretreatment of step (a) is effected at a solids concentration of about 5 to about 30% W/W.

* * * * *